United States Patent [19]

Harris et al.

[11] 4,310,762
[45] Jan. 12, 1982

[54] CALORIMETRIC TRACE ANALYSIS BY LASER INDUCED THERMAL LENS METHOD

[75] Inventors: Joel M. Harris; Norman J. Dovichi, both of Salt Lake City, Utah

[73] Assignee: University of Utah, Salt Lake City, Utah

[21] Appl. No.: 115,733

[22] Filed: Jan. 28, 1980

[51] Int. Cl.³ .............................................. G01J 1/00
[52] U.S. Cl. ................................... 250/343; 250/347
[58] Field of Search ............ 250/343, 344, 347, 352; 356/317, 318, 441, 442

[56] References Cited

U.S. PATENT DOCUMENTS

| | | | |
|---|---|---|---|
| 3,436,964 | 4/1969 | Dolin et al. | 250/343 |
| 4,048,499 | 9/1977 | Kreuzer | 250/344 |
| 4,061,918 | 12/1977 | Preier et al. | 250/343 |

Primary Examiner—Alfred E. Smith
Assistant Examiner—Janice A. Howell
Attorney, Agent, or Firm—Trask & Britt

[57] ABSTRACT

A technique for detecting very small quantities of particular materials by absorption of visible, ultraviolet or infrared light from a laser source is disclosed. The technique takes advantage of the thermal lens effect, i.e., a thermally induced alteration of the index of refraction, which occurs whenever a laser beam is passed through an absorbing medium, especially fluids. A converging beam derived from a coherent, collimated beam, e.g., a laser beam in the infrared, visible, or ultraviolet light range, is passed through a reference cell. The converging beam is slightly modified by a change in the index of refraction due to the thermal lens effect occurring within the reference cell. The modified beam is passed through a sample cell containing the identical medium as that in said reference cell with an additional material therein sought to be identified. The reference cell and sample cell are located at points in the beam path such that any modification in the beam caused by a change in the index of refraction of the medium in the reference cell is cancelled by the same medium in the sample cell. Any detectable modification in the beam, e.g., expansion (or divergence), as it evolves from the sample cell is due to the thermal lens effect caused by the material sought to be identified.

14 Claims, 5 Drawing Figures

CALORIMETRIC TRACE ANALYSIS BY LASER INDUCED THERMAL LENS METHOD

BACKGROUND OF THE INVENTION

1. Field

This invention relates to calorimetric or spectrometric devices for detecting materials in gaseous, liquid or solid samples by impingement of laser beams thereon to discern changes in the temperature of said fluid by absorption of energy from said laser beam by such materials sought to be identified, said materials selectively absorbing energy of different wavelengths.

2. Prior Art

The thermal lens effect results whenever a laser beam is impinged onto a material, e.g., a liquid, solid or gas, which is at least slightly transparent to said beam whereby a certain portion of the energy is absorbed, increasing the temperature of the material especially in the center of the beam. The temperature increase generally results in a lowering of the refractive index, producing a diverging lens effect which defocuses the beam.

The thermal lens effect, first reported by Gordon et al, *J. Appl. Phys.* 36, 3 (1965), is produced in an experimental arrangement similar to normal single beam absorption spectrometry. The major difference is that laser radiation passing through a sample is detected only at the center of the beam by restricting the field of view of the detector with a pinhole. The sample causes a loss of radiation from the beam center by thermal defocussing; that is, light absorbed by the sample is converted to heat by non-radiative relaxation and increases the temperature of the solvent by an amount which is greatest at the center of the beam. This temperature increase results in a lowering of the refractive index, producing a negative lens which defocusses the beam.

If the path from the laser to the sample is initially blocked and then opened with a shutter, the thermal lens takes a finite time to build up. A steady state condition is obtained when the rate of laser heating equals the rate of heat loss due to the thermal conductivity of the solvent and the finite temperature rise. The buildup of the lens can take place on time scales from tens of microseconds to hundreds of milliseconds depending on the thermal conductivity of the solvent and the radius of the laser beam through the sample.

The intensity measured at the beam center, $I(t)$, will initially ($t=0$) reflect only the Beer's law response of the sample. After sufficient time, when a steady state temperature difference is reached, the intensity of the detector, $I(\infty)$, depends on the optical arrangement of the system. An optimum configuration which minimizes $I(\infty)$ is obtained when the sample is placed one confocal length beyond the beam waist formed by a long focal length lens. In this configuration, using $TEM_{oo}$ laser beam to probe a sample whose length, l, is sufficiently small ($l << 2\pi w_o^2/\lambda$, where $w_o$ is the beam waist, n is the refractive index and $\lambda$ is the laser wavelength), the following expression governs the initial and final intensities (2):

$$\frac{I(o) - I(\infty)}{I(\infty)} = -\frac{2.303\, P(dn/dT)}{\lambda \cdot k} \cdot A \quad (1)$$
$$= 2.303 \cdot E \cdot A$$

where P is the laser power in watts, dn/dT is the change in solvent refractive index with temperature (usually negative), A is the sample absorbance, $\lambda$ is the laser wavelength, k is the thermal conductivity in watts/cm K and E is the enhancement of this effect relative to Beer's law behavior. This expression assumes that all of the absorbed light is converted into heat. If the quantum yield of fluorescence is finite, then a correction term which includes the quantum yield and Stokes shift may be applied. The choice of solvent for a determination governs the enhancement, E, that one realizes for a particular laser power. Table I lists several solvents, their pertinent thermo-optical properties and the enhancement per unit laser power (in mW) taking as the wavelength $\lambda = 632.8$ nm from the visible He:Ne laser transition.

TABLE 1

Thermo-optical Properties of Solvents For Thermal Lens Measurements[a]

| Solvent | k (mW/cm °K.) | $10^4 \cdot$ dn/dT (°K.$^{-1}$) | E/P[b] (mW$^{-1}$) |
|---|---|---|---|
| CCl$_4$ | 1.02 | 5.8 | 8.93 |
| Benzene | 1.44 | 6.4 | 7.02 |
| Acetone | 1.60 | 5.0 | 4.97 |
| Methanol | 2.01 | 3.9 | 3.06 |
| Water | 6.11 | 0.8 | 0.21 |

[a]Data taken from Solimini. J. Appl. Physics 37, 3314 (1966).
[b]Enhancement per unit laser power in milliwatts, $\lambda = 632.8$ nm.

To minimize the time constant of the effect and while maximizing the response, the thermal lens is generally measured in an optical configuration shown in FIG. 1. The laser beam of divergence, $\theta$, enters from the left through a lens, 11, having focal length, f. This produces a minimum beam radius, $w_o \leq f \cdot \theta$.

The sample is placed at a position, 13, relative to the beam waist. The influence of the position has been derived by Hu and Whinnery, *Applied Optics* 12, 72 (1973), for a thin sample such that w does not change over the cell path.

$$\frac{I(o) - I(\infty)}{I(\infty)} = -\frac{2.303\, P(dn/dT)}{K} \left[ \frac{2w_o(w^2 - w_o^2)^{\frac{1}{2}}}{w^2} \right] \cdot A \quad (2)$$

The expression inside the brackets maximizes to a value of 1 when $w = w_o\sqrt{2}$ which reduced Equation 2 to Equation 1. To obtain the thermal lens effect versus a more useful experimental parameter, z, the expression, $$w^2 = w_o^2 + \frac{z^2\lambda^2}{\pi^2 w_o^2} \quad (3)$$

is substituted for $w^2$ in Equation (2) to give $$\frac{I(o) - I(\infty)}{I(\infty)} = -\frac{2.303\, P(dn/dT)}{\lambda K} \frac{2z\, z_c}{z_c^2 + z^2} \cdot A \quad (4)$$

where $z_c$ is the confocal distance, $z_c = \pi w_o^2/\lambda$. The expression inside the brackets showing the all position dependence is plotted in FIG. 2 and has maxima and minima when $z = \pm z_c$.

U.S. Pat. No. 4,048,499 to Kreuzer employs an infrared laser beam of predetermined wavelength to produce heating of a sample, e.g., a liquid, which contains components which absorb energy from the laser beam. A thermal detector, such as a thermistor, is disposed in thermal energy exchanging relocation with the liquid sample which experiences a limited temperature increase due to energy absorption by components therein. The device of Kreuzer is limited in its sensitivity by the effectiveness of the thermistor and its failure to discriminate between absorption by components to be detected and background absorption by the liquid carrying medium, cell walls, etc.

OBJECTS OF THE INVENTION

It is an object of the instant invention to provide an effective analytical tool for accurately detecting very small amounts and concentrations of components in various media.

Another object of the invention is to provide an analytical device employing the thermal lens effect in a manner to disregard background effects.

A further object of the instant invention is to provide a calorimetric analytical device whereby measurements are obtained by determining the expansion of a laser beam.

SUMMARY OF THE INVENTION

A novel apparatus and process for identifying very minor amounts of components in a medium has been invented. A source of coherent, collimated light energy projects a beam of light, especially one in the infrared, ultraviolet and visible wavelength regions, through a lens or onto mirror means to cause convergence of said beam. The converging beam is passed through a reference cell containing a known medium, especially a fluid, which is transparent or weakly absorbing to said beam. The beam exiting such reference cell continues to converge until it reaches a waist region of narrow beam width. Thereafter, the beam diverges and is passed through a sample cell located substantially the same distance from the waist region as the reference cell.

The sample cell contains the same medium as found in the reference cell with an additional component, e.g., a solute in a liquid solvent or a minor constituent in a gaseous or solid sample, which is to be identified. The laser beam undergoes divergence as it passes through each cell due to the thermal lens effect. In the reference cell, any temperature increase is due to absorption of energy by the reference medium and any minor impurities and the like. In the sample cell, the same reference medium also contains components to be detected. Any temperature increase in the sample cell is due to the medium and minor impurities, as in the reference cell, plus heat caused from absorption of energy by the component or components to be identified or quantified.

Proper selection of location of the respective cells results in a cancelling of the effects of the carrier medium and minor impurities with the resulting beam divergence caused solely by absorption of energy by the component or components sought to be identified or quantified.

A significant advantage of the device of the instant invention is its usefulness as either a qualitative or quantitative analytical tool. Another advantage is that it is simple in construction and operation.

Figure 1:
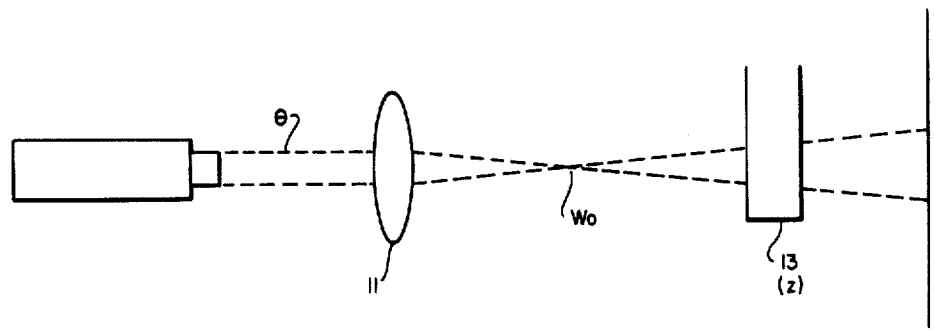
FIG. 1 is a sketch of a device which illustrates the thermal lens effect.
Figure 2:
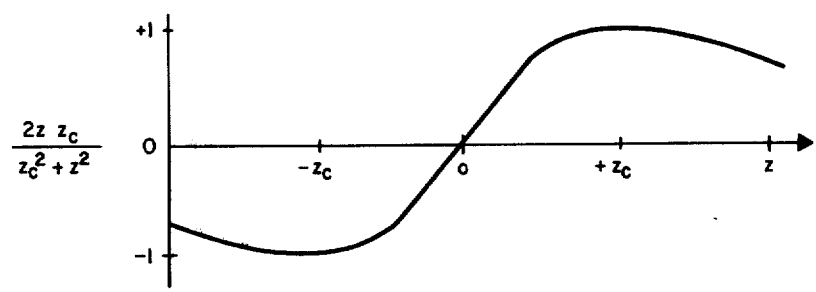
FIG. 2 is a graph illustrating the thermal lens effect as a condition of sample position.
Figure 3:
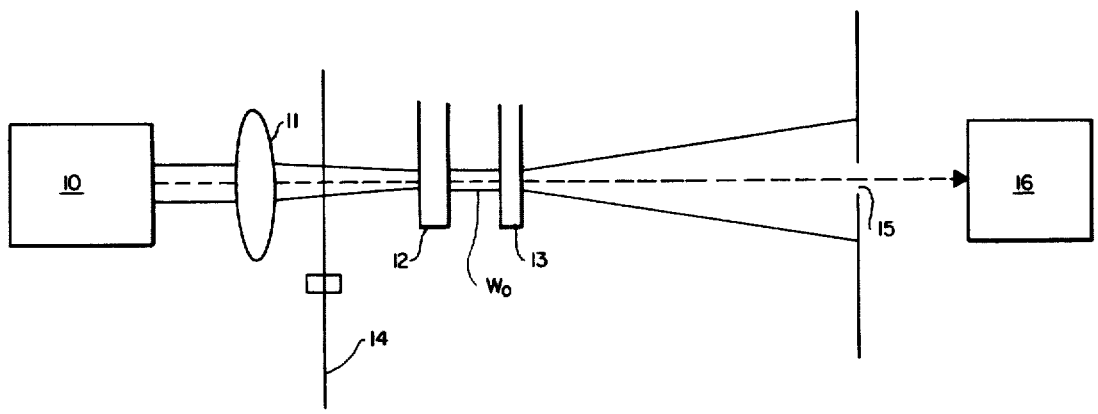
FIG. 3 is a sketch illustrating a differential thermal lens calorimetry device.

Further description of the invention may be facilitated by reference to the attached drawings. In FIG. 3 a beam of collimated, coherent light of selected wavelength, in the infrared, ultraviolet or visible range, is emitted from a laser 10. Such a laser frequency employs a lasing medium such as a $CO_2$ He:Ne, Argon, CO or the like. The minimum power useful for the purposes of this invention is about one milliwatt, while a preferred minimum power is about 4 mW. Although lasers with very high power outputs may be used, it is generally not required to use a laser with a power greater than 5 watts to obtain good results.

A lens 11 is placed in the path of the laser beam to cause convergence of the beam. A laser beam of a width of about $1.0 \times 10^{-3}$ cm to about $1.0 \times 10^{-1}$ cm is typical for this invention. The beam converges to a waist area having a width of about $1 \times 10^{-5}$ cm to about $1 \times 10^{-3}$ cm. A parabolic reflector could be used in place of lens 11.

A reference cell 12 is positioned in the converging laser beam a predetermined distance from Wo, the point of minimum beam waist. The reference cell is constructed of an inert, transparent material which interferes the least with the laser beam transmission. Glass, quartz and sapphire are preferred materials for the cell walls. The reference cell (which has parallel walls) is positioned at a slight angle to the axis of the laser beam to minimize interference patterns at the detector.

Cell dimensions may be varied depending upon laser power, beam width, fluid carried in cells and the nature of the component to be detected. Typical cell dimensions are as follows: 0.5 to 2.0 mm wall thickness, 0.5 to 2.0 cm cell depth or thickness, 2.0 to 5.0 cm height, 2.0 to 5.0 cm width. Cell wall thickness and cell depth or thickness are more important generally than cell height or width. Usually a minimum cell wall thickness and cell depth are preferred so long as the cell has structural integrity and the depth of sample exposed to the beam is sufficient to experience a thermal lens effect.

A second cell 13, a sample cell is located downstream of the minimum beam waist Wo about the same distance as the reference cell is upstream from Wo. The second cell is of the same construction and dimensions as the reference cell. Also, the second cell is slightly inclined to the direction of the beam transmission.

In practice, the reference cell is slightly farther from Wo than the sample cell inasmuch as some power is absorbed or reflected as the beam passes through the reference cell. The sample cell is located theoretically by calculating its proper position, as indicated hereinafter. The reference cell is then positioned empirically by placing a cell with the same material therein at the calculated position and then moving it, generally away from Wo, until the beam divergence caused by the reference cell is cancelled by the "sample" cell.

In the device illustrated in FIG. 3, a chopper 14 is utilized which interrupts light from the laser periodically. A lens effect is achieved in most media within a very short time after exposure, e.g., within a few microseconds to several milliseconds, depending upon the thermal conductivity of the medium. The thermal lens effect is a time-dependent phenomenon, as explained elsewhere herein. Generally, the lens effect dissipates or relaxes faster than it is created so the periods of "darkness" provided by the chopper 14 may be shorter in duration than the periods of illumination. A shutter or other device capable of interrupting the laser beam to produce bursts of energy for predetermined periods associated with predetermined periods of darkness may be utilized.

The beam produced by the laser is altered only by the material to be identified in the sample cell since the thermal lens effect of the other material in the sample and reference cells has a cancelling effect when the two cells are properly positioned. Thus, the light intensity charge passing through a pinhole 15 to a photo diode device 16 is measured to identify the unknown material in the sample cell. A photoelectrode array or vidicon tube may be substituted for the photo diode device to measure changes in beam intensity.

A determination of any change in beam intensity provides data which is proportional to changes in beam widths. A change in beam width will cause a corresponding change in radiation intensity at a given area within the beam width affected by the thermal lens effect. Thus, any change in the intensity of radiation passing through pinhole 15 can be interpreted. The degree of change becomes indicative of the material sought to be identified.

The position dependence is exploited in the instant invention to effect a differential thermal lens measurement capable of cancelling background absorption. A sample cell is placed one confocal distance, $Z_c$, beyond the minimum beam radius, while a reference cell is placed near a position one confocal distance, $-Z_c$, before the minimum beam radius. Due to the antisymmetric shape of the position dependence, a subtraction of the perturbations of the beam divergence by the two cells results such that:

$$\frac{I(o) - I(\infty)}{I(\infty)} = 2.303 \cdot E \cdot \delta A \quad (5)$$

when the enhancement, E, is the same for both cells (same solvent, same laser power), where $\delta A$ is the difference between the absorbance of the reference and sample materials. Generally, the laser power entering the sample cell is slightly smaller due to reflective losses at the reference cell. To maintain the differential response (equal enhancements), the reference cell may be positioned farther away from the minimum radius to reduce its effect on the beam divergence, by the position dependent term in Equation 4. A null position is found empirically.

The divergence of the beam caused by the components in the sample cell is measured after the elapse of a predetermined or preset time interval. Although beam divergence occurs over the entire beam radius, the index of refraction of the fluid changes most near the center of the beam. The beam divergence may be accurately measured and the quantity of energy-absorbing component determined.

Many materials, elements and components, are very selective energy-absorbers at particular wavelengths. Thus, by beaming energy of a selected wavelength into a pair of cells (each with the same sample carrier), the absorption of energy in the sample cell indicates that an element or compound known to absorb energy at that given wavelength is present.

EXAMPLE 1

A thermal lens calorimeter has been constructed to demonstrate the position dependence, Equation 4, and the differential response, Equation 5, with two identical samples in the beam. The particular apparatus used for this example is shown in FIG. 3. An argon ion laser producing 150-170 mW of optical power at 514.5 nm was used. A 40 cm plano-convex lens focusses the beam, and a single chopper blade on a slow dc motor blocks the beam for 0.25 sec. out of every 1.0 sec. The reference and sample cells are matched and have 1 mm thick glass walls and a 1.0 cm pathlength. The 1 mm pinhole and vacuum phototube detector are placed approximately 2 m beyond the sample cell. The intensities in the beam center, I(o) and I(oo), are sampled with an electronic circuit previously described by Dovichi and Harris, *Analytical Chemistry* 51, 728 (1979).

Figure 4:
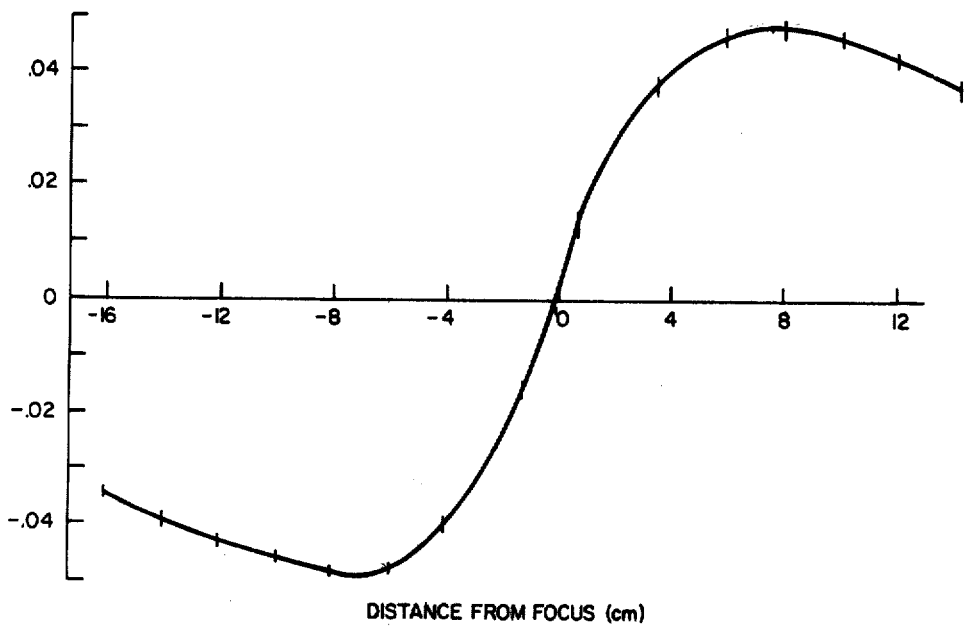
FIG. 4 is a graph illustrating positional dependence of a single cell thermal lens calorimetry device.
Figure 5:
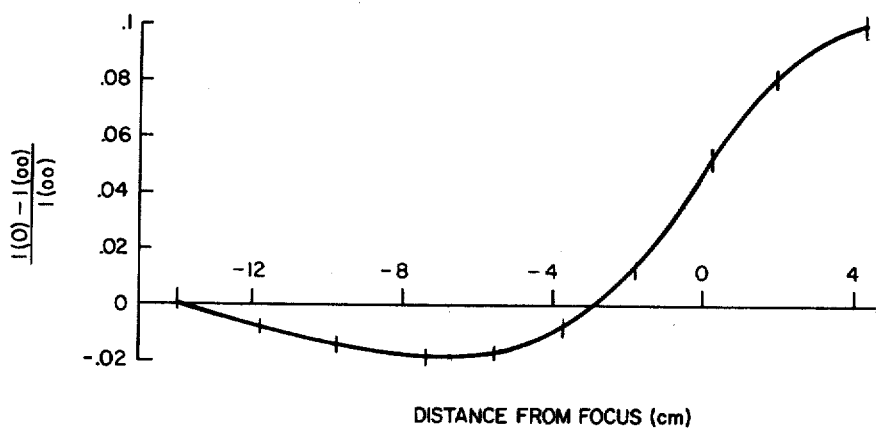
FIG. 5 is a graph illustrating the positional dependence of a double cell thermal lens calorimetry device.

To verify Equation 4, the reference cell is removed and the sample cell filled with a solution of phenophthalein in water having an absorbance, $A = 2 \times 10^{-3}$ cm$^{-1}$. The cell is moved about the focus, producing the results shown in FIG. 4. The solid curve through the points is a plot of Equation 4 with $Z_c = 7.2$ cm. To empirically observe a differential response for the paricular case where the absorbance of the sample and reference are equal ($\delta A = 0$), a reference cell is filled with the same solution as the sample cell. The sample cell was located at a position 7.2 cm beyond the focus and the position of the reference cell is varied as in FIG. 5. The null response is observed for 2 positions, approximately 2 cm and 13 cm before the focus.

EXAMPLE 2

The apparatus of Example 1 was also used to verify the differential response of Equation 5 and the resulting sensitivity of the apparatus. A determination of iron(II) as its complex with 1,10 phenathroline was carried out in a solvent mixture of 1:1 methanol:water. The reference cell containing solvent, 1,10 phenanthroline, and hydroxylamine was placed in the null position. To the sample cell, containing the same solvent, 1,10 phenanthroline and hydroxylamine, was added successive aliquots of a solution of ferric nitrate. Linear response to the addition of over 2 orders of magnitude iron to the sample cell was observed. A background absorbance, $A = 5.1 \times 10^{-5}$ cm$^{-1}$, was effectively eliminated allowing a limit of detection (95% confidence) of $A = 4.4 \times 10^{-7}$ cm$^{-1}$ indicative of $2.8 \times 10^{-12}$ g/ml of iron.

Those technical publications referenced herein are incorporated herein as those fully set forth.

The apparatus and method described herein are particularly advantageous because of their simplicity and accuracy. Although a laser emitting infrared radiation is generally preferred, any source generating a beam of coherent, collimated light may be utilized. The energy in said beam must be sufficient to create a thermal lens effect in the background medium, preferably a liquid or a gas, and in the material to be identified.

We claim:

1. A laser powered absorption apparatus comprising:
   laser means for generating a beam of radiation;
   beam convergence means located in the beam of radiation generated by said laser;
   first and second cell means for receiving a sample, said cells located beyond said beam convergence means and in alignment with one another and said beam convergence means so that said beam of converging radiation passes through said first cell and then through said second cell, said cells spaced from one another a predetermined distance;

beam width detection means located beyond said second cell and in alignment with said cells and said convergence means so that radiation passing through said second cell is received by said beam width detection means.

2. A method of identifying very small quantities of radiation-absorbing in a sample by absorption of radiation generated by a laser comprising:

generating a coherent, collimated beam of radiation of a predetermined wavelength absorbed by a material sought to be identified;

converging said coherent collimated beam of radiation;

passing said converging beam of radiation through a first sample at a point where said beam is still converging;

passing the beam of radiation as modified by said first sample through a second sample, said second sample being of the same composition as said first sample with very small quantities of additional materials therein to be identified;

measuring the change in beam width resulting from the change in index of refraction of said second sample caused by the localized increase in temperature of said second sample wherein a particular material in said second sample absorbs some of the radiation.

3. The laser powered absorption apparatus of claim 1 wherein said laser means generates a beam of infrared radiation.

4. The laser powered absorption apparatus of claim 1 wherein said beam convergence device is a lens.

5. The laser powered absorption apparatus of claim 3 wherein said beam of infrared radiation has a beam divergence of less than 1 rad.

6. The laser powered absorption apparatus of claim 1 wherein said beam width detection means is selected from the class consisting of photo diode arrays and vidicon tubes.

7. The laser powered absorption apparatus of claim 1 wherein said first and second cell means is adapted to receive samples of fluids.

8. The laser powered absorption apparatus of claim 7 wherein said fluid is a liquid.

9. The laser powered absorption apparatus of claim 1 wherein said second cell is located beyond the focal point of said convergence beam substantially the same distance as the first cell is located ahead of said focal point.

10. The method of claim 2 wherein the sample is the effluent from a chromatograph selected from the class of gas and liquid chromatographs.

11. The method of claim 2 wherein said coherent, collimated beam is of infrared radiation.

12. The method of claim 2 wherein said beam of radiation is passed through a focal point and is diverging before it is passed through a second sample.

13. The method of claim 11 wherein the width of the diverging beam passing through a second sample is substantially the same as the width of the converging beam passing through said first sample.

14. The method of claim 2 wherein said second sample is located beyond the focal point of said beam in reference to said first sample by moving a second sample identical in composition to said first sample along said beam until a null is obtained and thereafter replacing said second sample of the same composition with a sample of the same composition plus an unknown material to be identified.

* * * * *